United States Patent
Lynn

(10) Patent No.: US 12,276,644 B2
(45) Date of Patent: *Apr. 15, 2025

(54) DETECTION AND QUANTITATION OF GUANIDINOACETATE, CREATINE, AND CREATININE BY MASS SPECTROMETRY

(71) Applicant: Quest Diagnostics Investments LLC, Secaucus, NJ (US)

(72) Inventor: Thomas C. Lynn, San Clemente, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/509,590

(22) Filed: Nov. 15, 2023

(65) Prior Publication Data

US 2024/0085386 A1  Mar. 14, 2024

Related U.S. Application Data

(63) Continuation of application No. 16/056,240, filed on Aug. 6, 2018.

(60) Provisional application No. 62/545,349, filed on Aug. 14, 2017.

(51) Int. Cl.
| | |
|---|---|
| *G01N 30/72* | (2006.01) |
| *G01N 30/04* | (2006.01) |
| *G01N 30/88* | (2006.01) |
| *G01N 33/70* | (2006.01) |

(52) U.S. Cl.
CPC ......... *G01N 30/7266* (2013.01); *G01N 30/72* (2013.01); *G01N 30/7233* (2013.01); *G01N 30/88* (2013.01); *G01N 33/70* (2013.01); *G01N 2030/045* (2013.01); *G01N 2030/884* (2013.01); *G01N 2560/00* (2013.01)

(58) Field of Classification Search
None
See application file for complete search history.

(56) References Cited

U.S. PATENT DOCUMENTS

| 11,860,141 B2 * | 1/2024 | Lynn ................. G01N 30/88 |
| 2012/0288498 A1 | 11/2012 | Sooknanan et al. |

FOREIGN PATENT DOCUMENTS

| CN | 1532544 A | 9/2004 |
| JP | 2015232563 A | 12/2015 |
| WO | 2011048173 A1 | 4/2011 |

OTHER PUBLICATIONS

Carling, et al. ("Simultaneous determination of guanidinoacetate, creatine and creatinine in urine and plasma by un-derivatized liquid chromatography-tandem mass spectrometry." Annals of clinical biochemistry 45.6 (2008): 575-584).*

Young, et al. ("Quantification of creatine and guanidinoacetate using GC-MS and LC-MS/MS for the detection of cerebral creatine deficiency syndromes." Current protocols in human genetics 54.1 (2007): 17-3).*

BaróN-Sola, et al. ("First evidence of accumulation in cyanobacteria of guanidinoacetate, a precursor of the toxin cylindrospermopsin." Chemosphere 119 (2015): 1099-1104).*

(Continued)

*Primary Examiner* — Andrew Smyth
(74) *Attorney, Agent, or Firm* — Foley & Lardner LLP

(57) ABSTRACT

Provided are methods for detecting or determining the amount of guanidinoacetate (GAA), creatine, and creatinine by mass spectrometry.

17 Claims, 6 Drawing Sheets

(56) References Cited

OTHER PUBLICATIONS

Yasuda, et al. ("Simultaneous determination of creatinine, creatine, and guanidinoacetic acid in human serum and urine using liquid chromatography-atmospheric pressure chemical ionization mass spectrometry." Analytical biochemistry 253.2 (1997): 231-235).*
Baron-Sola, A., et al., "First Evidence of Accumulation in Cyanobacteria of Guanidinoacetate, A Precursor of the Toxin Cylindrospermopsin," Chemosphere, 2015, vol. 119, pp. 1099-1104.
Bodamer O.A., et al., "Analysis of Guanidinoacetate and Creatine by Isotope Dilution Electrospray Tandem Mass Spectrometry", Clinica Chimica Acta, 2001, vol. 308(1-2), pp. 173-178.
Boenzi S. et al., "Simultaneous Determination of Creatine and Guanidinoacetate in Plasma by Liquid Chromatography-Tandem Mass Spectrometry (LC-MS/MS)," Journal of Pharmaceutical and Biomedical Analysis, 2011, vol. 56 (4), pp. 792-798.
Carducci C., et al., "Quantitative Determination of Guanidinoacetate and Creatine In Dried Blood Spot by Flow Injection Analysis-electrospray Tandem Mass Spectrometry" Clinica Chimica Acta, vol. 364(2006), pp. 180-187.
Carling R.S., et al., "Simultaneous Determination of Guanidinoacetate, Creatine and Creatinine in Urine and Plasma by Un-Derivatized Liquid Chromatography-Tandem Mass Spectrometry," Annals of Clinical Biochemistry, Nov. 2008, vol. 45 (Pt 6), pp. 575-584.
Cognat S. et al., "Determination of Guanidinoacetate and Creatine in Urine and Plasma by Liquid Chromatography-Tandem Mass Spectrometry," Clinical Chemistry, Aug. 2004, vol. 50 (8), pp. 1459-1461.
Extended European Search Report for Application No. EP18846681. 7, mailed on Mar. 11, 2021, 8 pages.
Final Office Action mailed Apr. 19, 2022 for U.S. Appl. No. 16/056,240, filed Aug. 6, 2018.
Final Office Action mailed Nov. 28, 2022 for U.S. Appl. No. 16/056,240, filed Aug. 6, 2018.
Final Office Action mailed on Dec. 9, 2019 for U.S. Appl. No. 16/056,240, filed Aug. 6, 2018.
Final Office Action mailed on Feb. 22, 2021 for U.S. Appl. No. 16/056,240, filed Aug. 6, 2018.
Haas D., et al., "Diagnosis and Therapeutic Monitoring of Inborn Errors of Creatine Metabolism and Transport Using Liquid Chromatography-Tandem Mass Spectrometry in Urine, Plasma and CSF," Gene, Elsevier, Amsterdam, NI, Jan. 15, 2014, vol. 538(1), pp. 188-194.
International Search Report and Written Opinion for Application No. PCT/US2018/045790, mailed on Nov. 19, 2018.
Non-Final Office Action mailed on Jul. 14, 2020 for U.S. Appl. No. 16/056,240, filed Aug. 6, 2018.
Non-Final Office Action mailed on May 14, 2019 for U.S. Appl. No. 16/056,240filed on 06August2018.
Non-Final Office Action mailed on Sep. 16, 2022 for U.S. Appl. No. 16/056,240, filed Aug. 6, 2018.
Non-Final Office Action mailed on Aug. 31, 2021 for U.S. Appl. No. 16/056,240, filed Aug. 6, 2018.
Noolen L.V., et al., "Simultaneous Determination of Guanidinoacetate, Creatine and Creatinine by Liquid Chromatography-Tandem Mass Spectrometry: A Diagnostic Toot for Creatine Deficiency Syndromes in Body Fluids and a Perspective Use on Cultured Fibroblasts", Annals Of Clinical Biology, Jul. 2013, vol. 71(4), pp. 429-437.
"Spectrum CCMSLIB00000577918 for GUANIDINOACETATE" retrieved from http://mona.fiehnlab.ucdavis.edu/spectra/display/CCMSLIB00000577918 on Jun. 9, 2020 (Year:2016).
Prieto J. A., et al., "Determination of Creatine and Guanidinoacetate by GC-MS: Study of Their Stability in Urine at Different Temperatures," Clinical Biochemistry, Jan. 2009, vol. 42 (1-2), pp. 125-128.
Yasuda M., et al., "Simultaneous Determination of Creatinine, Creatine, and Guanidinoacetic Acid in Human Serum and Urine Using Liquid Chromatography-Atmospheric Pressure Chemical Ionization Mass Spectrometry" Analytical Biochemistry, 1997, vol. 253, pp. 231-235.
Young S., et al., "Quantification of Creatine and Guanidinoacetate Using GC-MS and LC-MS/MS for the Detection of Cerebral Creatine Deficiency Syndromes," Current Protocols in Human Genetics, Jul. 2007, Supplement 54, Chapter 17, pp. 17.3.1-17.3.18.
Extended European Search Report for Application No. 23215199.3, mailed on Mar. 13, 2024, 9 Pages.

* cited by examiner

DETECTION AND QUANTITATION OF GUANIDINOACETATE, CREATINE, AND CREATININE BY MASS SPECTROMETRY

CROSS-REFERENCE TO RELATED PATENT APPLICATIONS

This application is a continuation of U.S. application Ser. No. 16/056,240, filed Aug. 6, 2018, which claims benefit of U.S. Provisional Application No. 62/545,349, filed Aug. 14, 2017, each of which is incorporated by reference herein in its entirety.

BACKGROUND OF THE INVENTION

Three human disorders characterized by deficiencies of L-arginine:glycine amidinotransferase (AGAT), guanidinoacetate methyltransferase (GAMT), and the X-linked creatine transporter (SLC6A8) cause cerebral creatine deficiency syndromes (CCDS). They are underdiagnosed because the presenting clinical features (e.g., psychomotor delay, failure to thrive, intellectual disability, seizures, autistic behaviors, spasticity, and movement abnormalities) are non-specific features. Brain creatine content is corrected with oral supplementation of creatine in AGAT and GAMT. The diagnosis is dependent upon the measurement of guanidinoacetate (GAA), creatine, and creatinine in urine and plasma. Elevated or decreased concentrations of these individual analytes in urine or plasma can differentiate the 3 diseases.

There's a need for an accurate and sensitive assay for guanidinoacetate (GAA), creatine, and creatinine.

SUMMARY OF THE INVENTION

Provided herein are methods for detecting or determining the amount of guanidinoacetate (GAA), creatine, and creatinine in a sample by mass spectrometry, including tandem mass spectrometry.

In certain embodiments, the methods provided herein are for detecting or determining the amount of guanidinoacetate (GAA), creatine, and creatinine comprising (a) purifying GAA, creatine, and creatinine in the sample; (b) ionizing GAA, creatine, and creatinine in the sample; and (c) detecting or determining the amount of the GAA, creatine, and creatinine ion(s) by mass spectrometry; wherein the amount of the GAA, creatine, and creatinine ion(s) is related to the amount of GAA, creatine, and creatinine in the sample.

In certain embodiments, the methods provided herein are for detecting or determining the amount of guanidinoacetate (GAA) comprising (a) purifying GAA in the sample; (b) ionizing GAA in the sample; and (c) detecting or determining the amount of the GAA ion(s) by mass spectrometry; wherein the amount of the GAA ion(s) is related to the amount of GAA in the sample.

In certain embodiments, the methods provided herein are for detecting or determining the amount of creatine comprising (a) purifying GAA, creatine, and creatinine in the sample; (b) ionizing creatine in the sample; and (c) detecting or determining the amount of the creatine ion(s) by mass spectrometry; wherein the amount of the creatine ion(s) is related to the amount of creatine in the sample.

In certain embodiments, the methods provided herein are for detecting or determining the amount of creatinine comprising (a) purifying creatinine in the sample; (b) ionizing creatinine in the sample; and (c) detecting or determining the amount of the creatinine ion(s) by mass spectrometry; wherein the amount of the creatinine ion(s) is related to the amount of creatinine in the sample.

In some embodiments, guanidinoacetate (GAA), creatine, and creatinine are underivatized prior to mass spectrometry.

In some embodiments, the sample is urine or serum or plasma. In a preferred embodiment, the sample is urine. In some embodiments, the sample is whole blood. In some embodiments, the sample is saliva.

In some embodiments, purifying provided herein comprises liquid chromatography. In some embodiments, the liquid chromatography comprises high performance liquid chromatography (HPLC).

In some embodiments, purifying provided herein comprises solid phase extraction (SPE).

In some embodiments, the ionization comprises electrospray ionization (ESI). In some embodiments, the ionization comprises ionizing in positive mode. In some embodiments, the ionization comprises ionizing in negative mode.

In some embodiments, methods provided herein further comprise adding an internal standard. In some embodiments, the internal standard is isotopically labeled.

In certain embodiments, the limit of quantitation of the methods is less than or equal to 1 mg/L. In some embodiments, the limit of quantitation of the methods is less than or equal to 0.9 mg/L. In some embodiments, the limit of quantitation of the methods is less than or equal to 0.8 mg/L. In some embodiments, the limit of quantitation of the methods is less than or equal to 0.7 mg/L. In some embodiments, the limit of quantitation of the methods is less than or equal to 0.6 mg/L. In some embodiments, the limit of quantitation of the methods is less than or equal to 0.5 mg/L. In some embodiments, the limit of quantitation of the methods is less than or equal to 0.4 mg/L. In some embodiments, the limit of quantitation of the methods is less than or equal to 0.3 mg/L.

In certain embodiments, the limit of detection of the methods is less than or equal to 1 mg/L. In some embodiments, the limit of detection of the methods is less than or equal to 0.9 mg/L. In some embodiments, the limit of detection of the methods is less than or equal to 0.8 mg/L. In some embodiments, the limit of detection of the methods is less than or equal to 0.7 mg/L. In some embodiments, the limit of detection of the methods is less than or equal to 0.6 mg/L. In some embodiments, the limit of detection of the methods is less than or equal to 0.5 mg/L. In some embodiments, the limit of detection of the methods is less than or equal to 0.4 mg/L. In some embodiments, the limit of detection of the methods is less than or equal to 0.3 mg/L. In some embodiments, the limit of detection of the methods is less than or equal to 0.2 mg/L. In some embodiments, the limit of detection of the methods is less than or equal to 0.1 mg/L.

In some embodiments said ionizing comprises generating a guanidinoacetate (GAA) precursor ion with the mass/charge ratio of 118.1±0.5. In some embodiments, the method further comprises generating one or more fragment ions with the mass/charge ratio of 72.1±0.5. In some embodiments, said ionizing comprises generating a creatine precursor ion with the mass/charge ratio of 132.1±0.5. In some embodiments, the method further comprises generating one or more fragment ions with the mass/charge ratio of 90.1±0.5. In some embodiments, said ionizing comprises generating a creatinine precursor ion with the mass/charge ratio of 114.1±0.5. In some embodiments, the method further comprises generating one or more fragment ions with the mass/charge ratio of 44.1±0.5.

In some embodiments, the methods may include adding an agent to the sample in an amount sufficient to deproteinate the sample.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Samples are purified herein by various means to allow removal of one or more interfering substances, e.g., one or more substances that would interfere with the detection of selected analyte parent and daughter ions by mass spectrometry.

As used herein, the term "test sample" refers to any sample that may contain analyte. As used herein, the term "body fluid" means any fluid that can be isolated from the body of an individual. For example, "body fluid" may include blood, plasma, serum, bile, saliva, urine, tears, perspiration, and the like.

As used herein, the term "derivatizing" means reacting two molecules to form a new molecule. Derivatizing agents may include isothiocyanate groups, dinitro-fluorophenyl groups, nitrophenoxycarbonyl groups, and/or phthalaldehyde groups, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr. A* 854: 23-35 (1999); see also, U.S. Pat. No. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 35 µm. As used in this context, the term "about" means ±10%. In a preferred embodiment the column contains particles of about 60 µm in diameter.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means ±10%. In a preferred embodiment the analytical column contains particles of about 4 µm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification", "limit of quantitation" or "LOQ" refers to the point where measurements become quantitatively meaningful. The analyte response at this LOQ is identifiable, discrete and reproducible with a precision of 20% and an accuracy of 80% to 120%.

As used herein, the term "limit of detection" or "LOD" is the point at which the measured value is larger than the uncertainty associated with it. The LOD is defined arbitrarily as 2 standard deviations (SD) from the zero concentration.

As used herein, an "amount" of analyte in a body fluid sample refers generally to an absolute value reflecting the mass of analyte detectable in volume of body fluid. However, an amount also contemplates a relative amount in comparison to another analyte amount. For example, an amount of analyte in a body fluid can be an amount which is greater than or less than a control or normal level of analyte normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.5 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
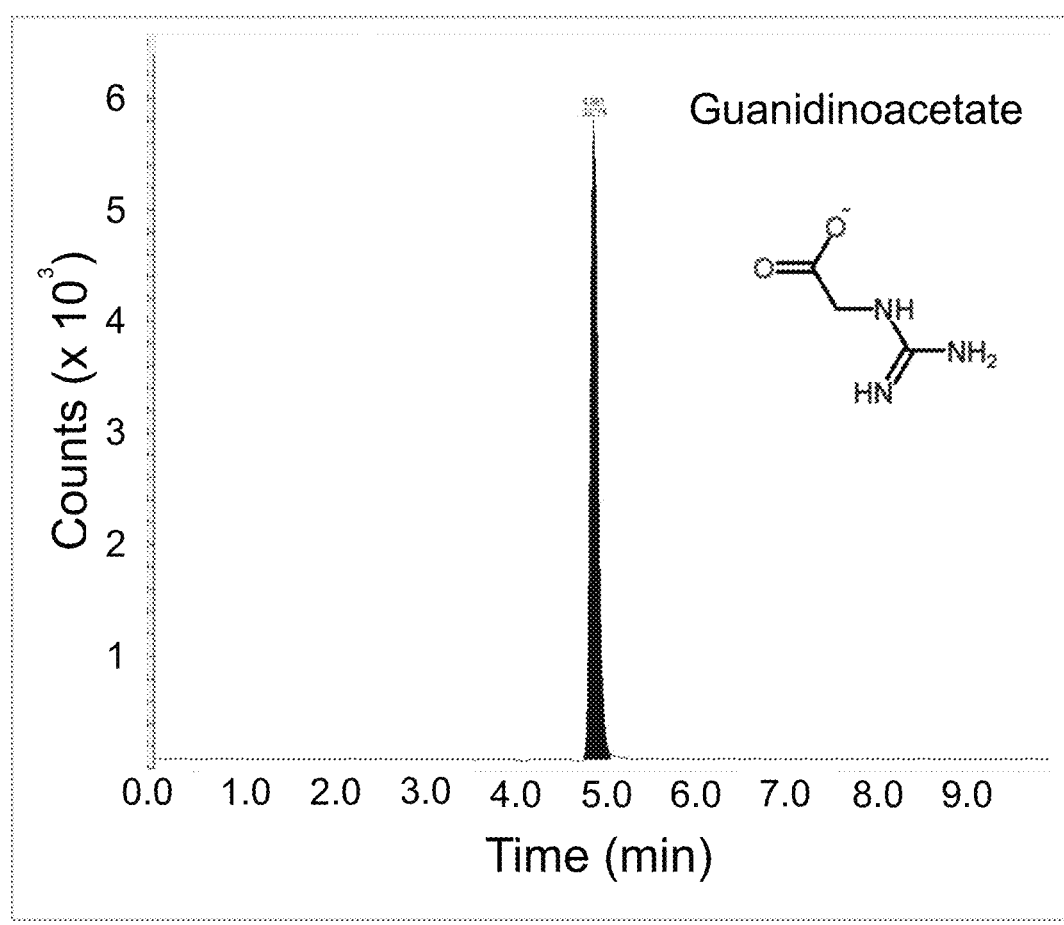
FIG. 1 shows a typical chromatogram of guanidinoacetate standard/calibrator.
Figure 2:
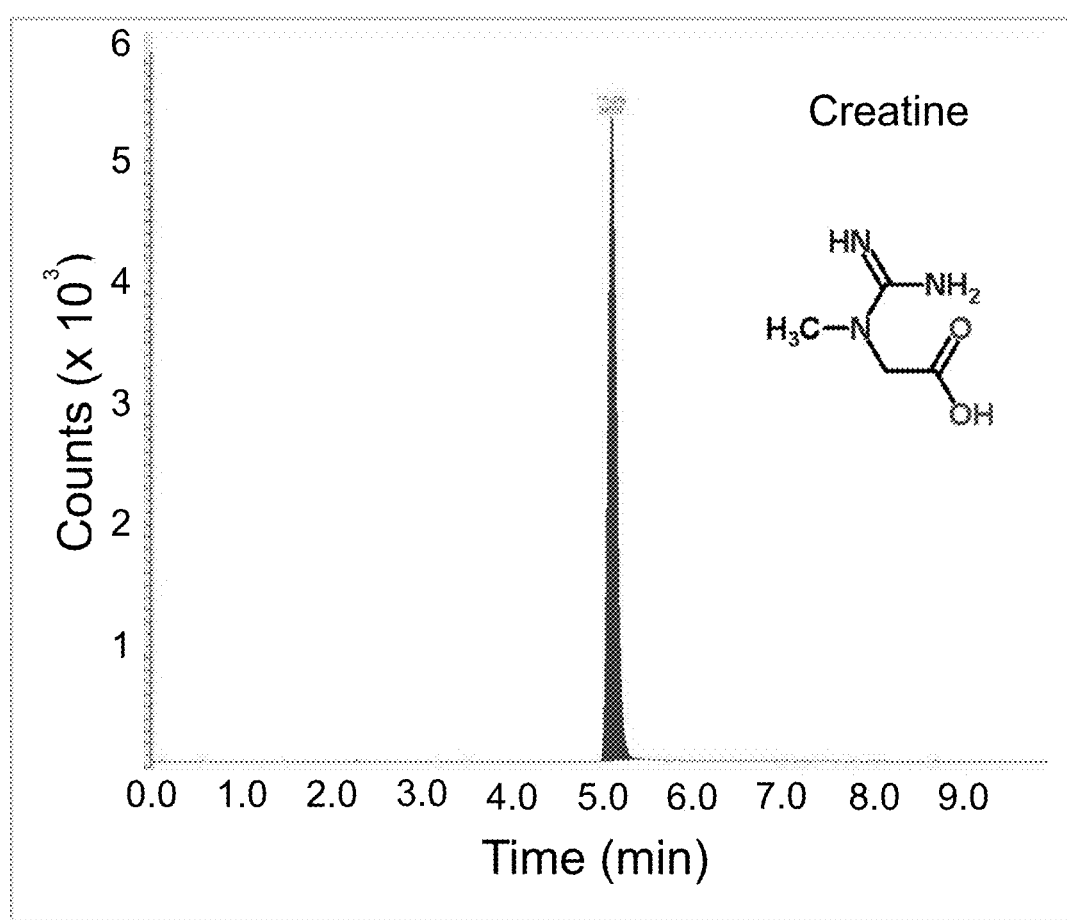
FIG. 2 shows a typical chromatogram of creatine standard/calibrator.
Figure 3:
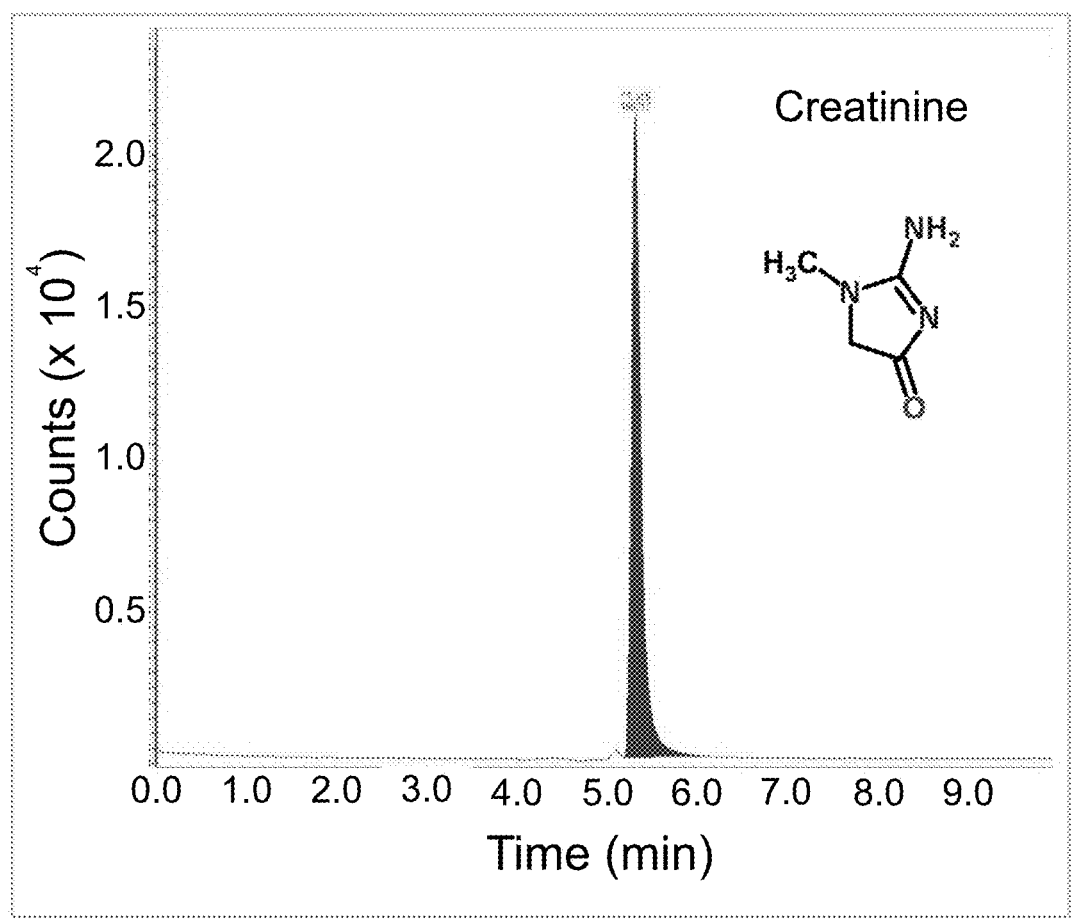
FIG. 3 shows a typical chromatogram of creatinine standard/calibrator.
Figure 4:
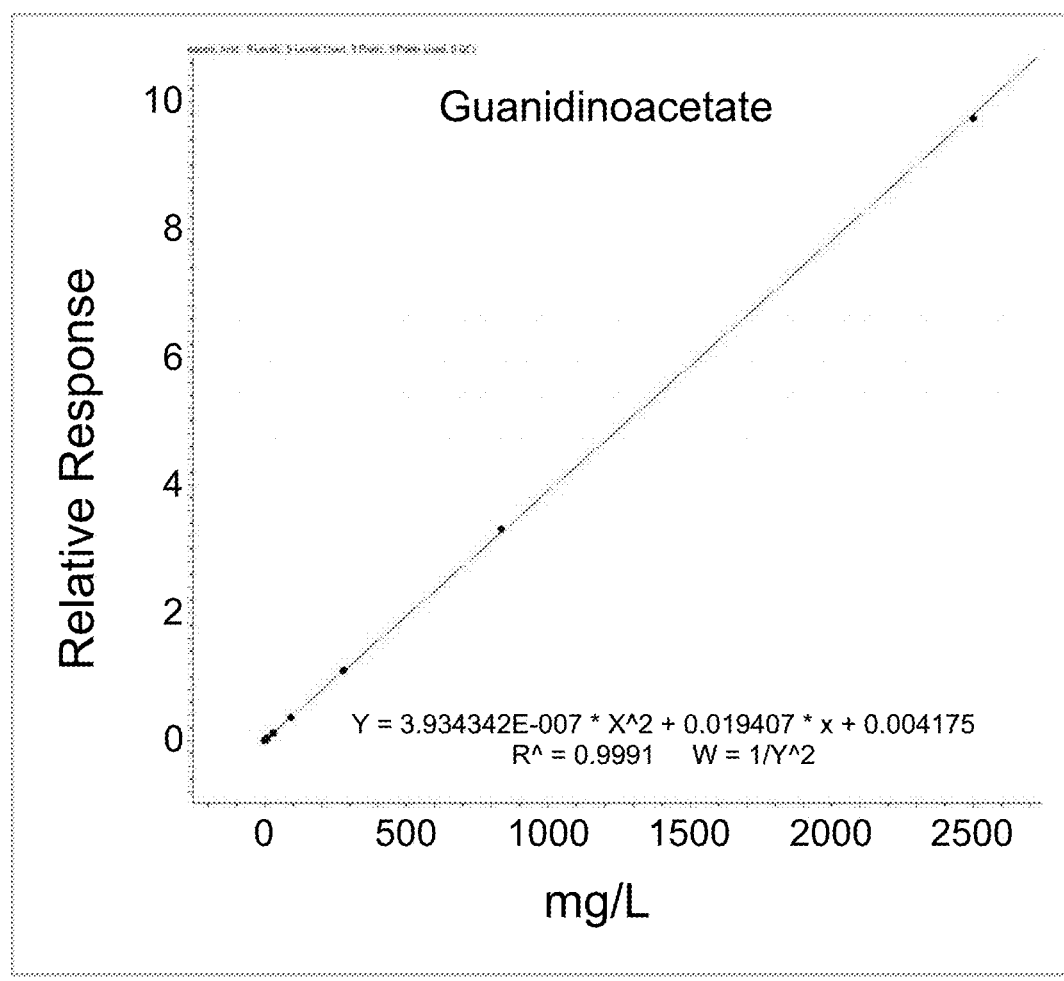
FIG. 4 shows a guanidinoacetate calibration curve including 9 data points from 0.4 to 2500 mg/L.
Figure 5:
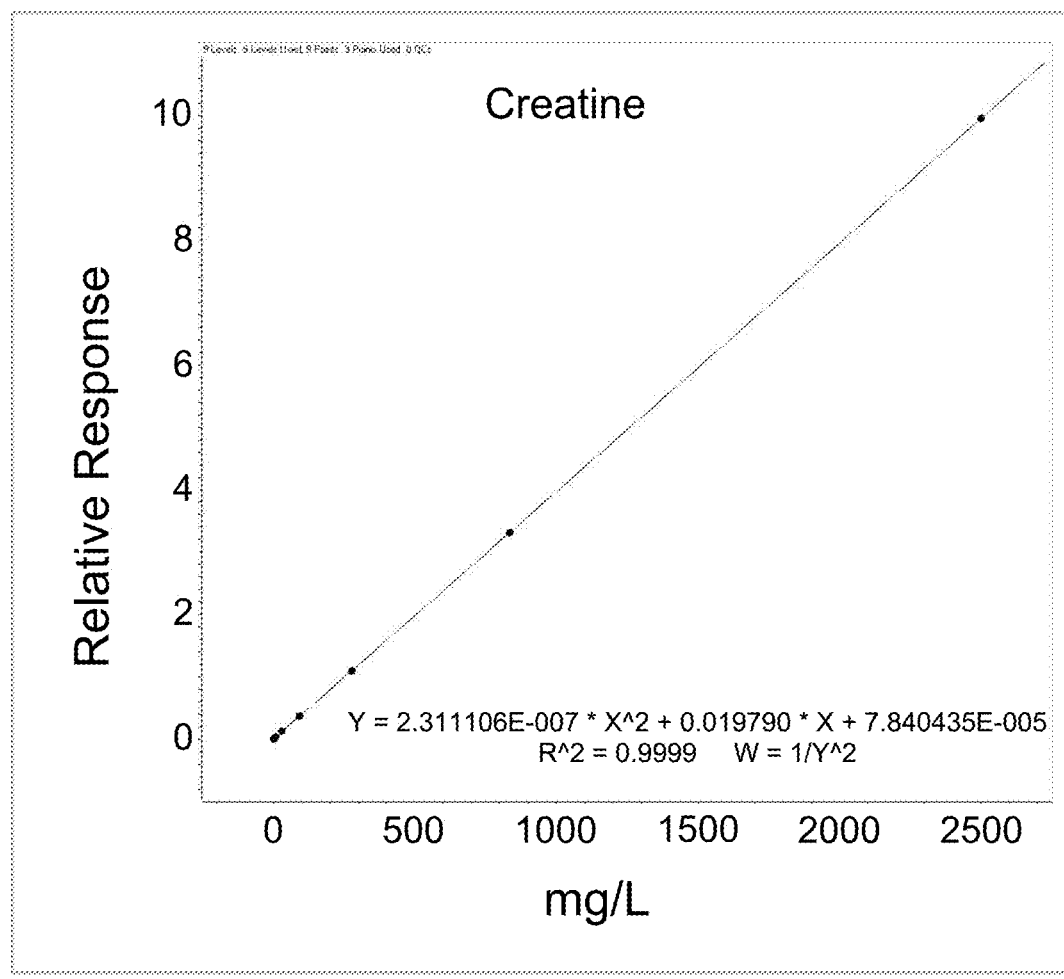
FIG. 5 shows a creatine calibration curve including 9 data points from 0.4 to 2500 mg/L.
Figure 6:
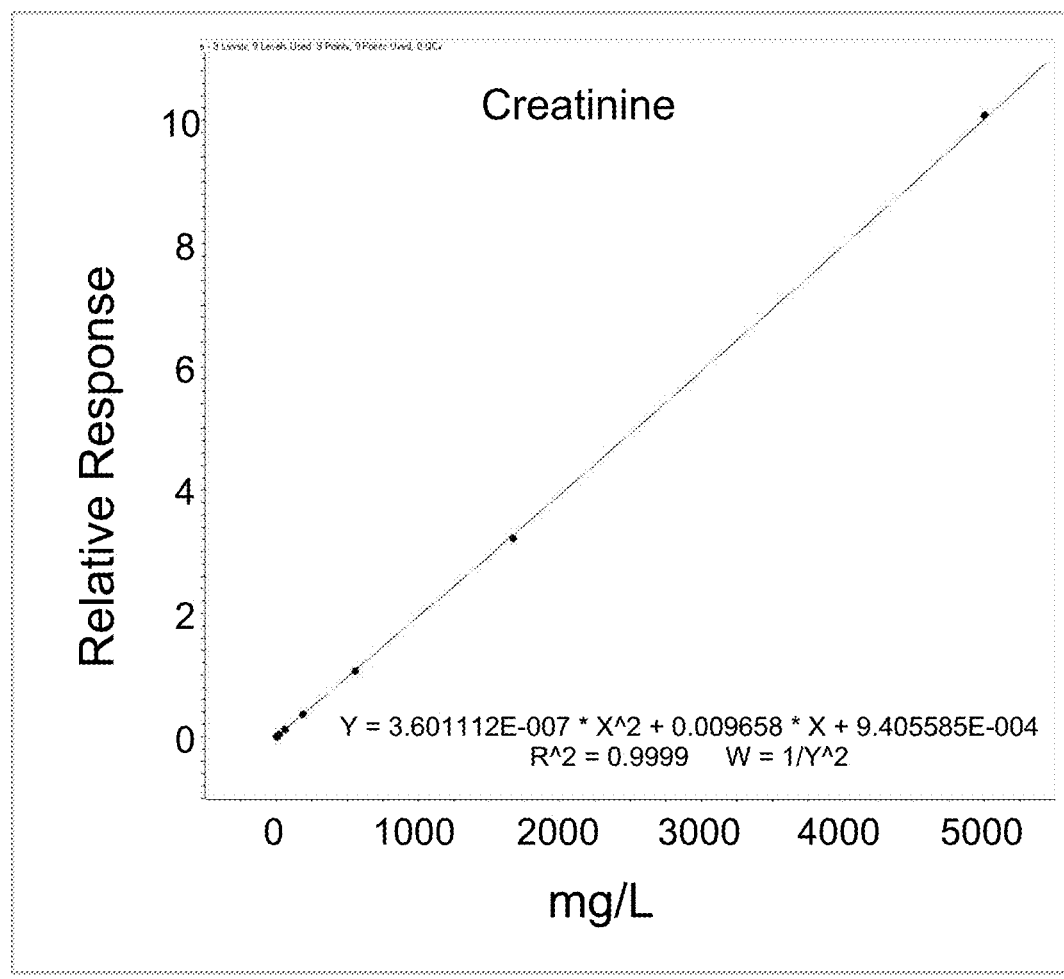
FIG. 6 shows a creatinine calibration curve including 9 data points from 0.8 to 5000 mg/L.

The cerebral creatine deficiency syndromes (CCDS), inborn errors of creatine metabolism, include the two creatine biosynthesis disorders (guanidinoacetate methyltransferase [GAMT] deficiency and L-arginine:glycine amidinotransferase [AGAT or GATM] deficiency), and the X-linked creatine transporter [SLC6A8] deficiency. Intellectual disability and seizures are common to all three CCDS. The majority of individuals with GAMT deficiency have a behavior disorder that can include autistic behaviors and self-mutilation; a significant proportion have pyramidal/extrapyramidal findings. Onset is between the ages of three months and three years. The phenotype of SLC6A8 deficiency in affected males ranges from mild intellectual disability and speech delay to severe intellectual disability, seizures, and behavior disorder, with age at diagnosis ranging from two to 66 years. Females heterozygous for SLC6A8 deficiency may have learning and behavior problems. Biochemical diagnosis of CCDS relies on the measurement of guanidinoacetate (GAA), creatine, and creatinine in urine and plasma.

In certain embodiments, the methods provided herein are for detecting or determining the amount of guanidinoacetate (GAA), creatine, and creatinine comprising (a) purifying GAA, creatine, and creatinine in the sample; (b) ionizing GAA, creatine, and creatinine in the sample; and (c) detecting or determining the amount of the GAA, creatine, and creatinine ion(s) by mass spectrometry; wherein the amount of the GAA, creatine, and creatinine ion(s) is related to the amount of GAA, creatine, and creatinine in the sample.

In certain embodiments, the methods provided herein are for detecting or determining the amount of guanidinoacetate (GAA) comprising (a) purifying GAA in the sample; (b) ionizing GAA in the sample; and (c) detecting or determining the amount of the GAA ion(s) by mass spectrometry; wherein the amount of the GAA ion(s) is related to the amount of GAA in the sample.

In certain embodiments, the methods provided herein are for detecting or determining the amount of creatine comprising (a) purifying GAA, creatine, and creatinine in the sample; (b) ionizing creatine in the sample; and (c) detecting or determining the amount of the creatine ion(s) by mass spectrometry; wherein the amount of the creatine ion(s) is related to the amount of creatine in the sample.

In certain embodiments, the methods provided herein are for detecting or determining the amount of creatinine comprising (a) purifying creatinine in the sample; (b) ionizing creatinine in the sample; and (c) detecting or determining the amount of the creatinine ion(s) by mass spectrometry; wherein the amount of the creatinine ion(s) is related to the amount of creatinine in the sample.

In some embodiments, guanidinoacetate (GAA), creatine, and creatinine are underivatized prior to mass spectrometry.

In some embodiments, the sample is urine or serum or plasma. In a preferred embodiment, the sample is urine. In some embodiments, the sample is whole blood. In some embodiments, the sample is saliva.

In some embodiments, purifying provided herein comprises liquid chromatography. In some embodiments, the liquid chromatography comprises high performance liquid chromatography (HPLC).

In some embodiments, purifying provided herein comprises solid phase extraction (SPE).

In some embodiments, the ionization comprises electrospray ionization (ESI). In some embodiments, the ionization comprises ionizing in positive mode. In some embodiments, the ionization comprises ionizing in negative mode.

In some embodiments, methods provided herein further comprise adding an internal standard. In some embodiments, the internal standard is isotopically labeled.

In certain embodiments, the limit of quantitation of the methods is less than or equal to 1 mg/L. In some embodiments, the limit of quantitation of the methods is less than or equal to 0.9 mg/L. In some embodiments, the limit of quantitation of the methods is less than or equal to 0.8 mg/L. In some embodiments, the limit of quantitation of the methods is less than or equal to 0.7 mg/L. In some embodiments, the limit of quantitation of the methods is less than or equal to 0.6 mg/L. In some embodiments, the limit of quantitation of the methods is less than or equal to 0.5 mg/L. In some embodiments, the limit of quantitation of the methods is less than or equal to 0.4 mg/L. In some embodiments, the limit of quantitation of the methods is less than or equal to 0.3 mg/L.

In certain embodiments, the limit of detection of the methods is less than or equal to 1 mg/L. In some embodiments, the limit of detection of the methods is less than or equal to 0.9 mg/L. In some embodiments, the limit of detection of the methods is less than or equal to 0.8 mg/L. In some embodiments, the limit of detection of the methods is less than or equal to 0.7 mg/L. In some embodiments, the limit of detection of the methods is less than or equal to 0.6 mg/L. In some embodiments, the limit of detection of the methods is less than or equal to 0.5 mg/L. In some embodiments, the limit of detection of the methods is less than or equal to 0.4 mg/L. In some embodiments, the limit of detection of the methods is less than or equal to 0.3 mg/L. In some embodiments, the limit of detection of the methods is less than or equal to 0.2 mg/L. In some embodiments, the limit of detection of the methods is less than or equal to 0.1 mg/L.

In some embodiments, the methods may include adding an agent to the sample in an amount sufficient to deproteinate the sample.

Suitable test samples include any test sample that may contain the analyte of interest. In some preferred embodiments, a sample is a biological sample; that is, a sample obtained from any biological source, such as an animal, a cell culture, an organ culture, etc. In certain preferred embodiments samples are obtained from a mammalian animal, such as a dog, cat, horse, etc. Particularly preferred mammalian animals are primates, most preferably male or female humans. Particularly preferred samples include blood, plasma, serum, hair, muscle, urine, saliva, tear, cerebrospinal fluid, or other tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum.

Sample Preparation for Mass Spectrometry

Methods that may be used to enrich in analyte relative to other components in the sample (e.g. protein) include for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Protein precipitation is one preferred method of preparing a test sample. Such protein purification methods are well known in the art, for example, Polson et al., *Journal of Chromatography B* 785:263-275 (2003), describes protein precipitation techniques suitable for use in the methods. Protein precipitation may be used to remove most of the protein from the sample leaving analyte in the supernatant. The samples may be centrifuged to separate the liquid supernatant from the precipitated proteins. The resultant supernatant may then be applied to liquid chromatography and subsequent mass spectrometry analysis. In certain embodiments, the use of protein precipitation such as for example, acetonitrile protein precipitation, obviates the need for high turbulence liquid chromatography (HTLC) or other on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography (HTLC).

In some preferred embodiments, HPLC, alone or in combination with one or more purification methods, may be used to purify analyte prior to mass spectrometry. In such embodiments samples may be extracted using an HPLC extraction cartridge which captures the analyte, then eluted and chromatographed on a second HPLC column or onto an analytical HPLC column prior to ionization. Because the steps involved in these chromatography procedures can be linked in an automated fashion, the requirement for operator involvement during the purification of the analyte can be minimized. This feature can result in savings of time and costs, and eliminate the opportunity for operator error.

It is believed that turbulent flow, such as that provided by HTLC columns and methods, may enhance the rate of mass transfer, improving separation characteristics. HTLC columns separate components by means of high chromatographic flow rates through a packed column containing rigid particles. By employing high flow rates (e.g., 3-5 mL/min), turbulent flow occurs in the column that causes nearly complete interaction between the stationary phase and the analyte(s) of interest. An advantage of using HTLC columns is that the macromolecular build-up associated with biological fluid matrices is avoided since the high molecular weight species are not retained under the turbulent flow conditions. HTLC methods that combine multiple separations in one procedure lessen the need for lengthy sample preparation and operate at a significantly greater speed. Such methods also achieve a separation performance superior to laminar flow (HPLC) chromatography. HTLC allows for direct injection of biological samples (plasma, urine, etc.). Direct injection is difficult to achieve in traditional forms of chromatography because denatured proteins and other biological debris quickly block the separation columns. HTLC also allows for very low sample volume of less than 1 mL, preferably less than 0.5 mL, preferably less than 0.2 mL, preferably 0.1 mL.

Examples of HTLC applied to sample preparation prior to analysis by mass spectrometry have been described elsewhere. See, e.g., Zimmer et al., *J. Chromatogr.* A 854:23-35 (1999); see also, U.S. Pat. Nos. 5,968,367; 5,919,368; 5,795,469; and 5,772,874. In certain embodiments of the method, samples are subjected to protein precipitation as described above prior to loading on the HTLC column; in alternative preferred embodiments, the samples may be loaded directly onto the HTLC without being subjected to protein precipitation. The HTLC extraction column is preferably a large particle column. In various embodiments, one of more steps of the methods may be performed in an on-line, automated fashion. For example, in one embodiment, steps (i)-(v) are performed in an on-line, automated fashion. In another, the steps of ionization and detection are performed on-line following steps (i)-(v).

Liquid chromatography (LC) including high-performance liquid chromatography (HPLC) relies on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples but a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays.

Various methods have been described for using HPLC for sample clean-up prior to mass spectrometry analysis. See, e.g., Taylor et al., *Therapeutic Drug Monitoring* 22:608-12 (2000); and Salm et al., *Clin. Therapeutics* 22 Supl. B:B71-B85 (2000).

One of skill in the art may select HPLC instruments and columns that are suitable for use with analyte. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, the HTLC may be followed by HPLC on a hydrophobic column chromatographic system. In certain preferred embodiments, a TurboFlow Cyclone P® polymer-based column from Cohesive Technologies (60 μm particle size, 50×1.0 mm column dimensions, 100 Å pore size) is used. In related preferred embodiments, a Synergi Polar-RP® ether-linked phenyl, analytical column from Phenomenex Inc (4 μm particle size, 150×2.0 mm column dimensions, 80 Å pore size) with hydrophilic endcapping is used. In certain preferred embodiments, HTLC and HPLC are performed using HPLC Grade Ultra Pure Water and 100% methanol as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In certain preferred embodiments, analyte or fragments thereof in a sample may be purified prior to ionization. In particularly preferred embodiments the chromatography is not gas chromatography.

Detection and Quantitation by Mass Spectrometry

In various embodiments, analyte or fragments thereof may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, analyte or a fragment thereof is ionized by heated electrospray ionization (HEST) in positive or negative mode. In alternative embodiments, analyte or a fragment thereof is ionized by electrospray ionization (ESI) or atmospheric pressure chemical ionization (APCI) in positive or negative mode.

After the sample has been ionized, the positively charged or negatively charged ions thereby created may be analyzed to determine a mass-to-charge ratio. Suitable analyzers for determining mass-to-charge ratios include quadrupole analyzers, ion traps analyzers, and time-of-flight analyzers. The ions may be detected using several detection modes. For example, selected ions may be detected i.e., using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of analyte. Methods of generating and using such standard curves are well known in the art and one of ordinary skill is capable of selecting an appropriate internal standard. For example, an isotope of analyte may be used as an internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In particularly preferred embodiments, analyte is detected and/or quantified using MS/MS as follows. The samples are subjected to liquid chromatography, preferably HPLC, the flow of liquid solvent from the chromatographic column enters the heated nebulizer interface of an MS/MS analyzer and the solvent/analyte mixture is converted to vapor in the heated tubing of the interface. The analyte is ionized by the selected ionizer. The ions, e.g. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of analyte. Precursor ions with the correct mass/charge ratios of analyte are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD). The fragment ions generated are passed into quadrupole 3 (Q3), where the fragment ions of analyte are selected while other ions are eliminated.

The methods may involve MS/MS performed in either positive or negative ion mode. Using standard methods well known in the art, one of ordinary skill is capable of identifying one or more fragment ions of a particular precursor ion of analyte that may be used for selection in quadrupole 3 (Q3).

If the precursor ion of analyte includes an alcohol or amine group, fragment ions are commonly formed that represent dehydration or deamination of the precursor ion, respectfully. In the case of precursor ions that include an alcohol group, such fragment ions formed by dehydration are caused by a loss of one or more water molecules from the precursor ion (i.e., where the difference in mass to charge ratio between the precursor ion and fragment ion is about 18 for the loss of one water molecule, or about 36 for the loss of two water molecules, etc.). In the case of precursor ions that include an amine group, such fragment ions formed by deamination are caused by a loss of one or more ammonia molecules (i.e. where the difference in mass to charge ratio between the precursor ion and fragment ion is about 17 for the loss of one ammonia molecule, or about 34 for the loss of two ammonia molecules, etc.). Likewise, precursor ions that include one or more alcohol and amine groups commonly form fragment ions that represent the loss of one or more water molecules and/or one or more ammonia molecules (i.e., where the difference in mass to charge ratio between the precursor ion and fragment ion is about 35 for the loss of one water molecule and the loss of one ammonia molecule). Generally, the fragment ions that represent dehydrations or deaminations of the precursor ion are not specific fragment ions for a particular analyte. Accordingly, in preferred embodiments of the invention, MS/MS is performed such that at least one fragment ion of analyte is detected that does not represent only a loss of one or more water molecules and/or a loss of one or more ammonia molecules from the precursor ion.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of analyte. As described above, the relative abundance of a given ion may be converted into an absolute amount of the original analyte, using calibration standard curves based on peaks of one or more ions of an internal molecular standard.

The following examples serve to illustrate the invention. These examples are in no way intended to limit the scope of the methods.

EXAMPLES

Example 1: Detection and Quantitation of GAA, Creatine, and Creatinine by Mass Spectrometry Samples were prepared by diluting urine 1:50 fold with ultrapure water. A minimum sample volume of 100 μL was used. Following dilution, samples were spiked with an internal standard mixture (deuterium-labeled creatinine, C13-labeled guanidinoacetate) and mixed. The diluted sample mix was injected onto an Agilent 1200 Series HPLC system using a reverse-phase column (Reversed Phase BDS 250×4.6 mm). HPLC mobile phases: 0.1% formic acid/acetonitrile.

Analysis was performed by positive electrospray ionization using an Agilent 6410 triple quadrupole mass spectrometer. The run time was 10 minutes.

The calibration curves showed consistency in reproducibility and linearity. The method provides linear results over a range of 0.4-2500 mg/L for guanidinoacetate and creatine and 0.8-5000 mg/L for creatinine. The lower limits of quantitation were 0.3 mg/L for guanidinoacetate and creatinine and 0.4 mg/L for creatine. Inter-assay coefficients of variation were 8.1 to 4.7% at 25-500 mg/L for guanidinoacetate, 9.9 to 6.1% at 25-500 mg/L for creatine, and 1.8 to 4.1% at 120-2300 mg/L for creatinine.

TABLE 1

Limit of quantitation and spiked recovery studies

| Analyte | LOQ (mg/L) | Mean Recovery (%)* |
| --- | --- | --- |
| Guanidinoacetate | 0.3 | 97 |
| Creatine | 0.4 | 101 |
| Creatinine | 0.3 | 102 |

TABLE 2

Guanidinoacetate Intra- and Inter-assay Precision and Accuracy

|  | Low | Medium | High |
|---|---|---|---|
| Intra-assay | | | |
| Mean (mg/L) | 26.3 | 105.0 | 511.0 |
| CV (%) | 1.2 | 0.9 | 0.6 |
| Accuracy (%) | 105.0 | 105.0 | 102.2 |
| N | 10 | 10 | 10 |
| Inter-assay | | | |
| Mean (mg/L) | 25.7 | 102.8 | 497.5 |
| CV (%) | 8.1 | 5.6 | 4.7 |
| Accuracy (%) | 102.8 | 102.8 | 99.5 |
| N | 31 | 31 | 31 |

Theoretical concentration of spiked material: 25, 100, and 500 mg/L for low, medium and high, respectively.

TABLE 3

Creatine Intra- and Inter-assay Precision and Accuracy

|  | Low | Medium | High |
|---|---|---|---|
| Intra-assay | | | |
| Mean (mg/L) | 27.5 | 107.0 | 509.8 |
| CV (%) | 1.3 | 1.3 | 0.9 |
| Accuracy (%) | 110.0 | 107.0 | 102 |
| N | 10 | 10 | 10 |
| Inter-assay | | | |
| Mean (mg/L) | 25.6 | 105.0 | 525.0 |
| CV (%) | 9.9 | 4.4 | 6.1 |
| Accuracy (%) | 102.4 | 105.0 | 105.0 |
| N | 31 | 31 | 31 |

Theoretical concentration of spiked material: 25, 100, and 500 mg/L for low, medium and high, respectively.

TABLE 4

Creatinine Intra- and Inter-assay Precision and Accuracy

|  | Low | Medium | High |
|---|---|---|---|
| Intra-assay | | | |
| Mean (mg/L) | 120.5 | 741.2 | 2318.1 |
| CV (%) | 2.1 | 2.2 | 1.2 |
| Accuracy (%) | 96.6 | 98.8 | 92.7 |
| N | 10 | 10 | 10 |
| Inter-assay | | | |
| Mean (mg/L) | 119.9 | 731.4 | 2295.2 |
| CV (%) | 1.8 | 2.0 | 4.1 |
| Accuracy (%) | 95.9 | 97.5 | 91.8 |
| N | 31 | 31 | 31 |

Theoretical concentration of spiked material: 125, 750, and 2500 mg/L for low, medium and high, respectively.

Precision/Sensitivity/Range

| | |
|---|---|
| Intra Assay Precision | GAA: |
| | Low Control: 1.2%  Mid Control: 0.9%  High Control: 0.6% |
| | Creatine: |
| | Low Control: 1.3%  Mid Control: 1.3%  High Control: 0.9% |
| | Creatinine |
| | Low Control: 2.1%  Mid Control: 2.2%  High Control: 1.2% |
| Inter Assay Precision | GAA: |
| | Low Control: 8.1%  Mid Control: 5.6%  High Control: 4.7% |
| | Creatine: |
| | Low Control: 9.9%  Mid Control: 4.4%  High Control: 5.6% |
| | Creatinine |
| | Low Control: 1.8%  Mid Control: 2.0%  High Control: 4.1% |
| Recovery Study | GAA: SD < Tea/4 for all samples |
| | Creatine: SD < Tea/4 for all samples |
| | Creatinine SD < Tea/4 for all samples |
| Analytical Sensitivity (Limit of Detection) | GAA: 2.84 nmol/mL |
| | Creatine: 0.22 nmol/mL |
| | Creatinine: 1.65 nmol/mL |
| Analytical Sensitivity (Limit of Quantitation) | GAA: 7.50 nmol/mL |
| | Creatine: 1.15 nmol/mL |
| | Creatinine: 2.34 nmol/mL |
| Linearity | GAA: 3 - 21348 nmol/mL |
| | Creatine: 3 - 19065 nmol/mL |
| | Creatinine: 7 - 44202 nmol/mL |
| Analytical Measurement Range (AMR) | GAA: 3 - 21348 nmol/mL |
| | Creatine: 3 - 19065 nmol/mL |
| | Creatinine: 7 - 44202 nmol/mL |
| Clinical Reportable Range (CRR) | GAA: 3 - 21348 nmol/mL |
| | Creatine: 3 - 19065 nmol/mL |
| | Creatinine: 7 - 44202 nmol/mL |

Measurements of these three analytes in urine allow for the biochemical diagnosis of CCDS. The ability to measure all three analytes directly in the urine, with a very simple method of sample preparation, is an improvement over previous methods involving derivatization and indirect calculations.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A method for determining an amount of guanidinoacetate (GAA), creatine, and creatinine in a single sample, the method comprising:
   purifying underivatized GAA, creatine, and creatinine in the single sample;
   ionizing the GAA, creatine, and creatinine in the single sample to produce one or more ion(s) of GAA, creatine, and creatinine;
   determining an amount of the ion(s) of GAA, creatine, and creatinine by mass spectrometry; wherein:
   a fragment ion with the mass/charge ratio of 72.1±0.5 is used to determine the amount of GAA ions; and
   the amount of the GAA, creatine, and creatinine ion(s) is related to the amount of GAA, creatine, and creatinine in the single sample.

2. The method of claim 1, wherein said purifying comprises liquid chromatography.

3. The method of claim 2, wherein said liquid chromatography comprises high performance liquid chromatography (HPLC).

4. The method of claim 1, wherein said GAA, creatine, and creatinine are underivatized.

5. The method of claim 1, wherein said ionization comprises electrospray ionization (ESI).

6. The method of claim 1, wherein said ionization comprises ionizing in positive mode.

7. The method of claim 1, further comprising adding an internal standard.

8. The method of claim 7, wherein said internal standard is isotopically labeled.

9. The method of claim 1, wherein the single sample is urine.

10. The method of claim 1, wherein the single sample is serum.

11. The method of claim 1, wherein the limit of quantitation of the methods is less than or equal to 0.4 mg/L.

12. The method of claim 1, wherein the limit of quantitation of the methods is less than or equal to 0.3 mg/L.

13. The method of claim 1, wherein said ionizing comprises generating a guanidinoacetate (GAA) precursor ion with the mass/charge ratio of 118.1±0.5.

14. The method of claim 1, wherein said ionizing comprises generating a creatine precursor ion with the mass/charge ratio of 132.1±0.5.

15. The method of claim 14, wherein the method further comprises generating one or more fragment ions with the mass/charge ratio of 90.1±0.5.

16. The method of claim 1, wherein said ionizing comprises generating a creatinine precursor ion with the mass/charge ratio of 114.1±0.5.

17. The method of claim 16, wherein the method further comprises generating one or more fragment ions with the mass/charge ratio of 44.1±0.5.

* * * * *